(12) United States Patent
Taylor et al.

(10) Patent No.: US 10,004,869 B2
(45) Date of Patent: Jun. 26, 2018

(54) GAS CONCENTRATOR WITH REMOVABLE CARTRIDGE ADSORBENT BEDS

(71) Applicants: Brenton Alan Taylor, Kenwood, CA (US); Peter Hansen, Santa Barbara, CA (US); John Russell Stump, Santa Barbara, CA (US); Patrick Fitzlindon Burgess, Dunedin, FL (US); Daniel Wayne Chin, Summerland, CA (US)

(72) Inventors: Brenton Alan Taylor, Kenwood, CA (US); Peter Hansen, Santa Barbara, CA (US); John Russell Stump, Santa Barbara, CA (US); Patrick Fitzlindon Burgess, Dunedin, FL (US); Daniel Wayne Chin, Summerland, CA (US)

(73) Assignee: Inogen, Inc., Goleta, CA (US)

( * ) Notice: Subject to any disclaimer, the term of this patent is extended or adjusted under 35 U.S.C. 154(b) by 553 days.

(21) Appl. No.: 14/142,613

(22) Filed: Dec. 27, 2013

(65) Prior Publication Data
US 2015/0182720 A1    Jul. 2, 2015

(51) Int. Cl.
*A61M 16/10*    (2006.01)
*A61M 16/00*    (2006.01)
(Continued)

(52) U.S. Cl.
CPC ......... *A61M 16/10* (2013.01); *B01D 53/0438* (2013.01); *B01D 53/0476* (2013.01); *A61M 16/107* (2014.02); *A61M 16/16* (2013.01); *A61M 2202/0208* (2013.01); *B01D 53/053* (2013.01); *B01D 2253/108* (2013.01); *B01D 2256/12* (2013.01); *B01D 2257/102* (2013.01); *B01D 2258/06* (2013.01); *B01D 2259/402* (2013.01); *B01D 2259/4533* (2013.01); *B01D 2259/4541* (2013.01)

(58) Field of Classification Search
CPC .......... A61M 16/10; A61M 2202/0208; A61M 16/107; A61M 16/00; A61M 16/0003; A61M 16/0063; A61M 16/1005; A61M 16/101; A61M 2016/1025; B01D 53/0476; B01D 53/0438; B01D 2259/4533; B01D 2253/108; B01D 2256/12; B01D 2258/06; B01D 2257/102; B01D 2259/402; B01D 2259/4541; B01D 53/053; B01D 53/047; B01D 53/0503
USPC .......................... 128/205.12, 204.18, 202.26
See application file for complete search history.

(56) References Cited

U.S. PATENT DOCUMENTS 4,094,775 A    6/1978   Mueller
4,302,224 A *  11/1981  McCombs ......... B01D 53/0446
                                            55/DIG. 17
(Continued)

OTHER PUBLICATIONS

U.S. Appl. No. 13/066,716, filed Apr. 22, 2011, Taylor et al.

*Primary Examiner* — Jackie Tan-Uyen T Ho
*Assistant Examiner* — Joseph D Boecker
(74) *Attorney, Agent, or Firm* — Mark Rodgers

(57) ABSTRACT

A portable oxygen concentrator designed for medical use where the adsorbent beds, are designed to be replaced by a patient. The concentrator is designed so that the power supply and adsorbent bed mount is one module and the compressor and air filter are part of another module configured to provide a unitary cooling and air supply system. Replacement beds may be installed easily by patients, and all gas seals will function properly after installation.

14 Claims, 9 Drawing Sheets

(51) Int. Cl.
*A61M 16/16* (2006.01)
*B01D 53/04* (2006.01)
*B01D 53/047* (2006.01)
*B01D 53/053* (2006.01)

(56) References Cited

U.S. PATENT DOCUMENTS

| | | |
|---|---|---|
| 4,530,706 A | 7/1985 | Jones |
| 6,149,138 A | 11/2000 | Birdsell |
| 6,755,895 B2 | 6/2004 | Lomax et al. |
| 7,780,768 B2 * | 8/2010 | Taylor ................ B01D 53/0476 96/132 |
| 7,857,894 B2 * | 12/2010 | Taylor ................... A61M 16/10 128/200.24 |
| 8,894,751 B2 | 11/2014 | Galbraith et al. |
| 9,199,055 B2 | 12/2015 | Galbraith et al. |
| 2005/0045041 A1 | 3/2005 | Hechinger et al. |
| 2005/0103341 A1 | 5/2005 | Deane et al. |
| 2006/0048644 A1 * | 3/2006 | Dolensky ................ A62B 21/00 95/96 |
| 2006/0117957 A1 | 6/2006 | McCombs et al. |
| 2006/0174874 A1 | 8/2006 | Jagger et al. |
| 2007/0137487 A1 | 6/2007 | Whitley et al. |
| 2008/0053310 A1 * | 3/2008 | Bliss ...................... A61M 16/10 96/115 |
| 2008/0257145 A1 * | 10/2008 | Sprinkle ............ B01D 53/0407 95/22 |
| 2009/0277333 A1 * | 11/2009 | Sakurai ............. B01D 53/0407 96/150 |
| 2010/0052293 A1 * | 3/2010 | Brooks ..................... B62B 1/12 280/651 |
| 2012/0055475 A1 * | 3/2012 | Wilkinson ............. A61M 16/12 128/204.21 |
| 2012/0167883 A1 * | 7/2012 | Taylor et al. ............ 128/204.18 |
| 2012/0167886 A1 * | 7/2012 | Taylor ................... A61M 16/10 128/205.12 |
| 2012/0192864 A1 * | 8/2012 | Galbraith ............... B01D 53/02 128/203.12 |
| 2012/0266883 A1 * | 10/2012 | Taylor ................... A61M 16/10 128/205.12 |
| 2013/0213234 A1 * | 8/2013 | Thompson ............ A61M 16/10 96/108 |
| 2013/0299005 A1 * | 11/2013 | Enomoto .......... A61M 16/0816 137/78.1 |
| 2016/0022950 A1 * | 1/2016 | Taylor ................. A61M 16/101 96/111 |

* cited by examiner

US 10,004,869 B2

GAS CONCENTRATOR WITH REMOVABLE CARTRIDGE ADSORBENT BEDS

RELATED APPLICATIONS

Not Applicable

FEDERALLY SPONSORED RESEARCH

Not Applicable

SEQUENCE LISTING

Not Applicable

BACKGROUND OF THE INVENTION

The invention generally relates to gas concentrators, and more particularly relates to medical oxygen concentrators used by patients in the home care setting where cost and frequency of maintenance performed by a technician should be minimized.

The application of oxygen concentrators for therapeutic use is known, and many variants of such devices exist. A particularly useful class of oxygen concentrators is designed to be used in a patient's home or workplace without the assistance of a medical practitioner or caregiver. These home concentrators are typically referred to as stationary concentrators, as they are not designed to be carried by a patient, distinguishable from portable concentrators which are designed to be carried by a patient for most ambulatory activities. Most of these oxygen concentrators are based on Pressure Swing Adsorption (PSA), Vacuum Pressure Swing Adsorption (VPSA), or Vacuum Swing Adsorption (VSA) designs which feed compressed air to selective adsorption beds, sometimes also referred to as sieve beds. In a typical oxygen concentrator, the beds utilize a zeolite adsorbent to selectively adsorb nitrogen, resulting in pressurized, oxygen-rich product gas. This class of oxygen concentrator may also contain one or more systems to extend the service life of the equipment. These systems may include software algorithms to alter the PSA timing, input flow, or operating pressure to extend the performance of the adsorption beds as their capacity is reduced over its operating life as described in common inventors' prior disclosures U.S. Pat. No. 7,857,894 and its related applications incorporated in their entirety by reference. In these systems the adsorption beds may also include desiccant layers before the main adsorbent layer to remove water and other contaminants or dedicated water removal components such as membrane air dryers as described in common inventors' prior disclosures U.S. Pat. No. 7,780,768 and its related applications, incorporated in their entirety by reference.

The main elements in a typical home-use therapeutic oxygen concentrator are shown in FIG. 1. Air is draw in, and typically filtered, at air inlet 1 before being pressurized by compressor 2 to a pressure of 1.2 to 2.5 atmospheres. The pressurized air is directed by feed valve arrangement 9 through adsorbent beds 3. An exemplary adsorbent bed implementation, used in a concentrator design developed by the inventors, is two columns filled with a lithium exchanged zeolite adsorbent in the ratio of about 1 gram of adsorbent per 1-10 ml of oxygen produced. The pressurized air is directed through these adsorber bed columns in a series of steps which constitute a gas separation cycle, often a PSA cycle or some variation including vacuum instead of, or in conjunction with, compression yielding overall compression ratios of about 1.5:1 to 4.0:1. Although many different arrangements of adsorber vessels and gas separation cycles are possible, the result is that nitrogen is removed by the adsorbent material, and the resulting oxygen rich gas is routed 10 to a product gas storage device at 4. Some of the oxygen product gas can be routed back through the bed to flush out (purge) the adsorbed nitrogen to an exhaust 6. Generally multiple adsorbent beds, or columns in the exemplary device, are used so at least one bed may be used to make product while at least one other bed is being purged, ensuring a continuous flow of product gas. The purged gas is exhausted from the concentrator at the exhaust 6.

Such gas separation systems are known in the art, and it is appreciated that the gas flow control through the compressor and the adsorbent beds is complex and requires precise timing and control of parameters such as pressure, flow rate, and temperature to attain the desired oxygen concentration of 80% to 95% purity in the product gas stream. Accordingly, most modern concentrators also have a programmable controller 5, typically a microprocessor, to monitor and control the various operating parameters of the gas separation cycle. In particular, the controller controls the timing and operation of the various valves used to cycle the beds through feed, purge, and pressure equalization steps, which make up the gas separation cycle. Also present in oxygen concentrators is an output control system 7 which acts to ensure that the therapeutic output flow of oxygen is continuous and steady even during the pressure swings associated with the production of the oxygen. A typical oxygen concentrator will also contain a user/data interface 8 including elements such as an LCD display, alarm LEDs, audible buzzers, and control buttons. Portable oxygen concentrators would necessarily also include one or more battery packs for portable use.

To be conveniently used by an individual in a home or workplace environment needing therapeutic oxygen, the stationary home oxygen concentrators should be less than about 2100 cubic inches and preferably less than 1600 cubic inches in total volume, less than about 25 pounds and preferably less than 20 pounds in weight, and produce less than about 45 decibels of audible noise, while retaining the capacity to produce a flow of product gas adequate to provide for a patient's oxygen needs, usually a flow rate prescribed by a medical practitioner in about the range of 1 LPM to 5 LPM. Although stationary PSA based concentrators have been available for many years, such fixed site units may weigh 30-50 pounds or more, be several cubic feet in volume, and may produce sound levels greater than 45 dBA. Thus they are loud and difficult to move around. To achieve these beneficial improvements in noise and size/weight, improved home oxygen concentrators involve a significant amount of miniaturization and efficiency improvements, leading to smaller, more complex designs compared to older designs. System size, weight, and complexity may lead to fewer mitigative options or design choices against contamination and other wear and tear effects that can lead to an unacceptably short maintenance interval, and therefore require novel design features to achieve both the improvements in size and noise while maintaining adequate lifetime.

It is therefore necessary to design home oxygen concentrators such that zeolite contamination is handled in a manner that avoids costly or frequent maintenance by a field technician or equipment provider. The inventors have previously disclosed a system that achieves long sieve bed life by removing water prior to the feed gas as described in the above cited references. This approach may desirable for some portable oxygen concentrators where the beds are even smaller than a home based stationary system, but because of the cost involved, may not be appropriate to stationary home based system where the price point needs to be very low. It is therefore desirable to design a home oxygen concentrator that minimizes size and weight and cost as a function of oxygen output with commonly available commercial adsorbents such as Z12-07 manufactured by Zeochem or Oxysiv MDX manufactured by UOP. While eliminating water removal components such as membrane air dryers or pretreatment layers such as activated alumina or a NaX type zeolite will reduce the cost of the adsorbent beds it will also reduce the service life of the beds to an unacceptable level. Oxygen equipment used for Long Term Oxygen Therapy (LTOT) is optimally deployed for 3-5 years without any service requirements. Any service requirement within that time interval simply adds to the overall cost of the equipment, which substantially reverses any cost benefit gained by removing a membrane air dryer or pretreatment layer. Further, allowing sieve bed contamination without prevention or service may lead to providing 82-87% purity oxygen instead of 87-95% pure oxygen to the patient. To reduce the overall cost of delivering oxygen therapy, devices must be designed that do not require field service by a technician or equipment provider, and also minimize the cost, size, power consumption, and noise of the equipment that is used inside of the patient's home.

A typical adsorbent bed or adsorber is constructed of a column with an inlet port and an outlet port arranged at opposite ends. The adsorbers would typically be connected to the valve manifold of the concentrator through tubing or a direct manifold connection. Either prior art construction method resulted in a robust pneumatic connection that was only meant to be disconnected by a trained service technician who could access the internal components of the concentrator and disconnect or disassemble the inlet and outlet connections. Some columns, such as those that are adhesive bonded to an integrated manifold, may not be removable at all in a field service environment and must be replaced in combination with other system components to achieve zeolite replacement. Therefore user-replaceable adsorber beds are desirable and provide an approach that may increase the service life of a concentrator without the costly water removal components and without the need for factory or factory trained service. Techniques for producing a medical concentrator of the portable type with user replaceable adsorber beds are described in U.S. application Ser. Nos. 13/016,706 and 13/449,138 by common inventors and incorporated in their entirety by reference

BRIEF SUMMARY OF THE INVENTION

The invention is an improved stationary home oxygen concentrator, including a PSA/VPSA/VSA core section capable of mating with user replaceable adsorbers, the core section including:
 a housing
 a controller
 a user interface
 at least two user replaceable adsorber beds
 at least one compressor, air control valve, and air filter, making a PSA/VPSA/VSA oxygen system when mated with the user replaceable adsorbers
 a patient delivery apparatus The concentrator also includes a module of at least one AC-DC power supply and docking elements for the user replaceable beds. The concentrator includes another module including the compressor and an air blower. The blower, and air inlets and outlets are arranged to form a unitary cooling and acoustic damping air flow system drawing air in from one side of the housing over the beds and over the compressor and power supply while directing exhaust gas from the beds to the muffler and both exhaust and cooling air directed out of the housing on an opposite side from the inlet.

Preferably, the concentrator weighs less than 25 pounds, produces less than 50 dba acoustic noise when operating, and has an output gas flow of 5 lpm or less.

In some embodiments, the concentrator has an input to receive the output from an external rechargeable battery capable of running the concentrator for greater than 2 hours. The concentrator may in these embodiments be switched between operating from the internal AC-DC power supply and the external battery. The adsorbers and the power supply module may be enclosed in a lower housing component that has rubber vibration and noise isolating feet or wheels.

In other embodiments the DC power input may also include a communication bus to communicate state and power information to the microprocessor on the concentrator. The concentrator in some embodiments may also include a diagnostics interface.

In some embodiments, an inlet filter is mounted to the exterior of the concentrator (which may form an ornamental surface of the exterior). The inlet filter may also form a portion of a mount for a humidifier. The inlet to the inlet filter is preferably directed into the interior of the concentrator to reduce external noise sources and source air from filtered air that has passed through the gross particle filter. Preferably the chassis directs airflow over at least the compressor and the power supply and the inlet cooling air is directed over the adsorbent beds.

In some embodiments the compressor subchassis is interconnected to the chassis via rails to provide a high amount of surface engagement to distribute shock load and prevent breakage of the chassis.

In some embodiments, the intake silencer and exhaust muffler are a common structure. Preferably, the lower housing cover may be removed to access the replaceable adsorber beds In additional embodiments the detachable lower housing may be equipped with either rubber vibration isolation feet or wheels to increase ease of movement within a house and best fit a patient's mode of usage for the equipment.

BRIEF DESCRIPTION OF THE DRAWINGS

The understanding of the following detailed description of certain preferred embodiments of the invention will be facilitated by referring to the accompanying figures.

DETAILED DESCRIPTION OF THE INVENTION

Figure 1:
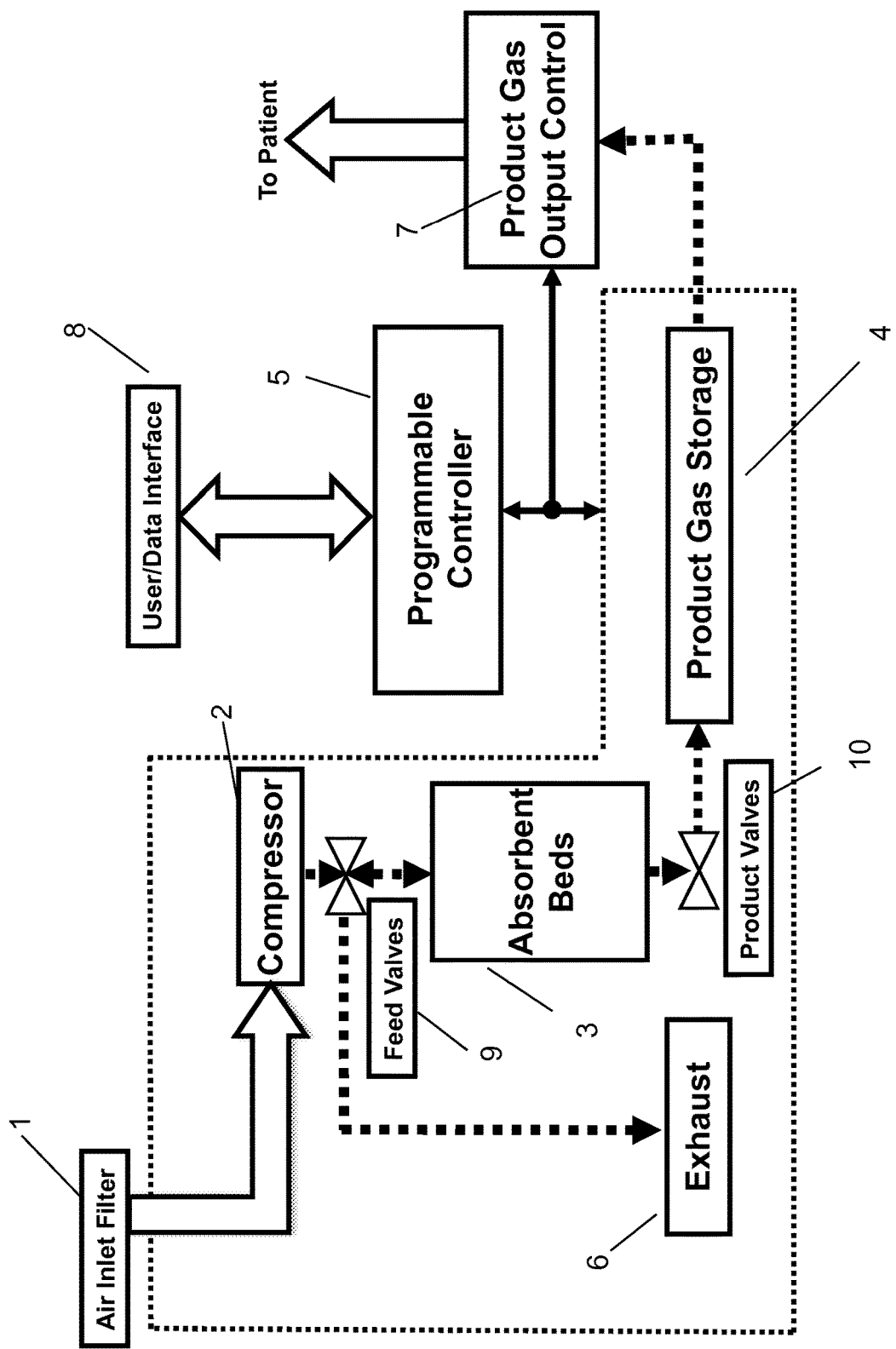
FIG. 1 shows the general elements of gas concentrators as applicable to certain embodiments of the invention.
Figure 2:
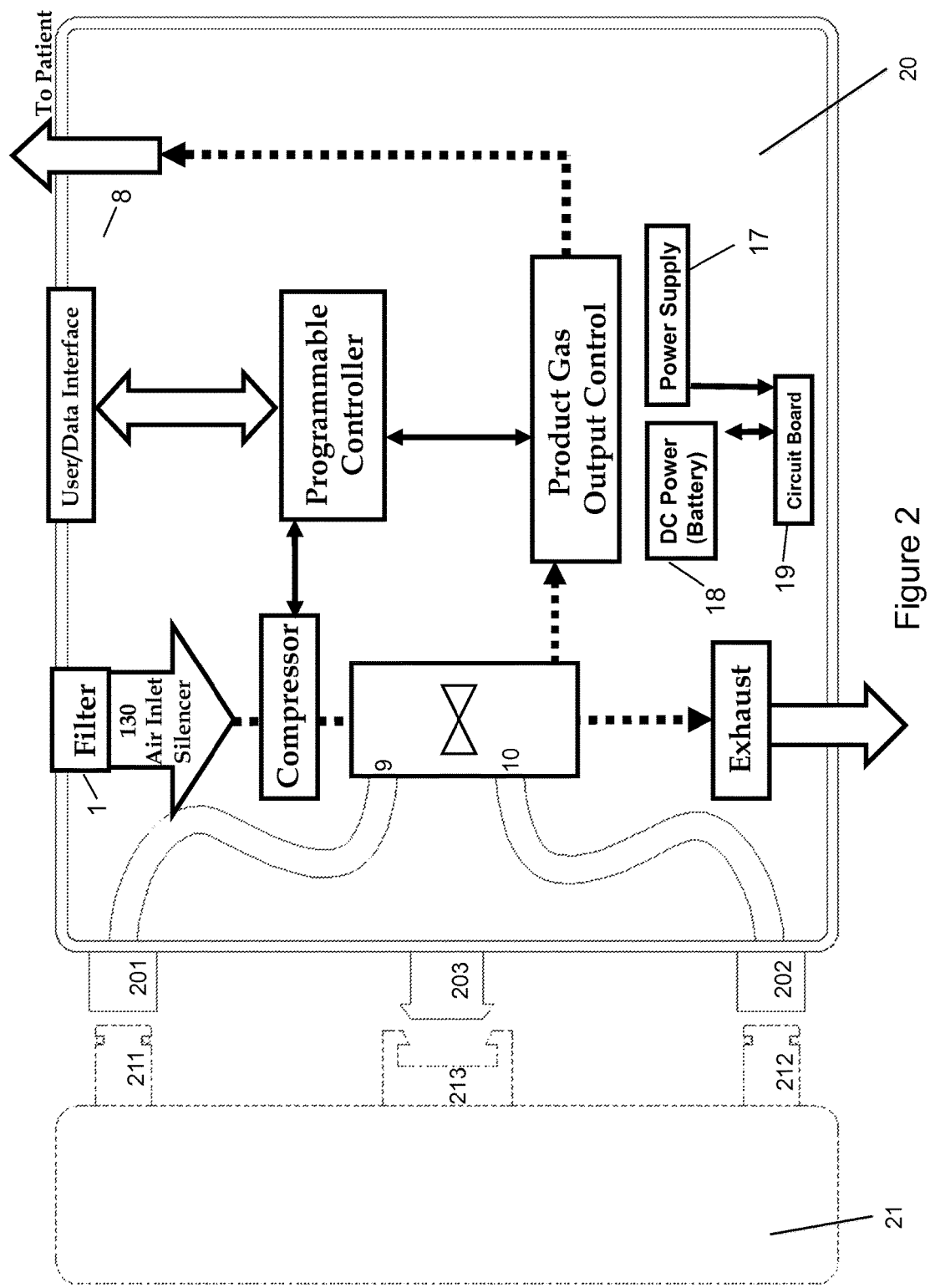
FIG. 2 illustrates the general concept where the concentrator platform is one portion and the user replaceable adsorber is another portion that together form a complete portable oxygen concentrator.

An ideal home stationary concentrator should still be light and compact enough for ease of movement and placement for use by a patient as opposed to a technician or caregiver. This class of equipment should preferably operate reliably for many years without the need for professional service and maintenance. These improved home oxygen concentrators are typically in the range of 10 to 20 lbs and produce from 0.3 to 5.0 LPM of oxygen. A particularly effective embodiment of the invention is an oxygen concentrator where the sieve bed cartridges or adsorbers can be removed and replaced without removing any fasteners or exposing internal operating components. FIG. 2 illustrates an embodiment of an exemplary concentrator suitable for the invention. One skilled in the art will appreciate that the alterations of design elements and arrangement of components from the exemplary design shown are possible to practice the novel elements of the invention. Thus the exemplary design shown is not limiting and the invention is limited only by the claims. The novel stationary concentrator incorporates multiple elements distinct from the portable concentrator with user replaceable beds described in application Ser. No. 13/016, 706, but also benefits from a replaceable bed design. As shown in FIG. 2 beds 21 interface to the other concentrator components 20 through feed gas connections 201 and 211, product gas connections 212 and 202 and are secured with retention mechanisms 213 and 203, examples of which are disclosed in application Ser. No. 13/016,706. The novel stationary concentrator has additional elements modularly attached to the core control and compressor section of the concentrator. The filter and power supply are located on the outside of the core structure while the adsorbent beds are internal to the outer casing to provide additional forced cooling air to pass over the adsorbent beds. The product gas connection 202 for each adsorber has been joined into a common element to reduce part count. Feed gas connections 201 and mating element 203 have also been integrated into a single element to reduce part count. A compressor inlet silencer 130 is added to the airflow system and the whole air intake/cooling system is a unitary design that achieves multiple objectives with a relatively small number of elements. In addition the novel stationary concentrator preferably operates with a power supply 17 which can be plugged into an AC power source (wall power) as well as optionally operating off of DC power 18, such as an external battery pack 18. The DC power option is particularly useful if the user's ambulatory needs include wheeled appliances such as walkers or wheelchairs, which can easily transport a concentrator in the size range envisioned, thus adding an element of portability to the novel stationary concentrator.

Figure 3:
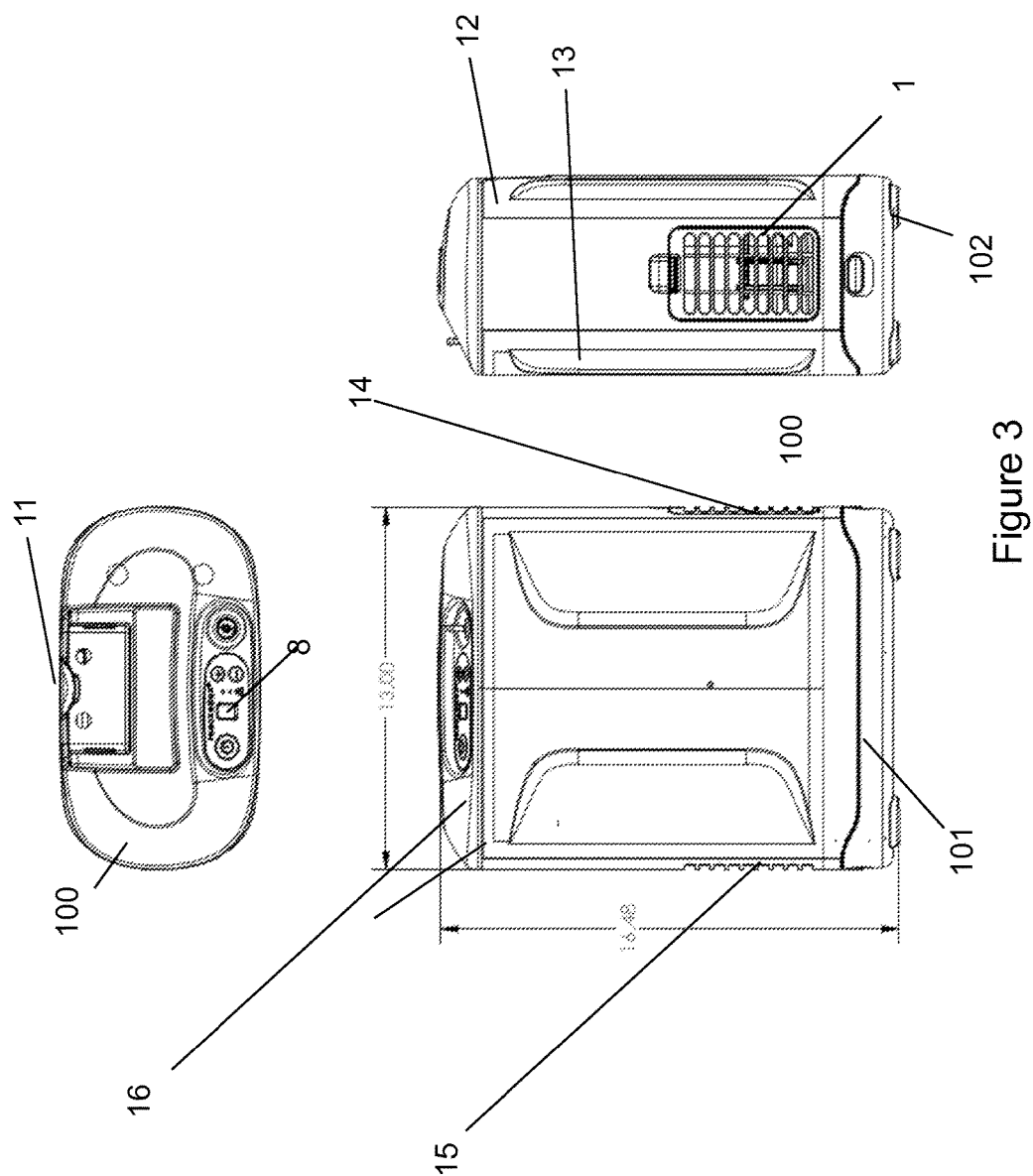
FIG. 3 shows an exemplary external layout of the concentrator.

Referring to FIG. 3, some exterior elements of an exemplary concentrator 100 are shown. The outer housing panels include a front and rear panel, 13 and 12, control panel 16 with an optional mount 11 for an external humidifier. Also shown are an intake panel 14, containing the gross particle filter 1 and exhaust panel 15 and a lower housing 101. In the exemplary concentrator design front 13 and rear 12 panels are removable by hidden screws that can be located when lower housing 101 is removed. The lower housing can be removed without tools to access the removable adsorbers. Lower, front, and rear panels can be removed during operation of the concentrator for easy service and troubleshooting. The front 13 and rear 12 panels are removable in such a way that they are the last elements of installation before the lower housing. Removing them exposes the internals of the concentrator while the intake housing 14 and the exhaust housing 15 continue to support the control panel housing 16. This exemplary arrangement is beneficial for repair and troubleshooting.

Figure 4:
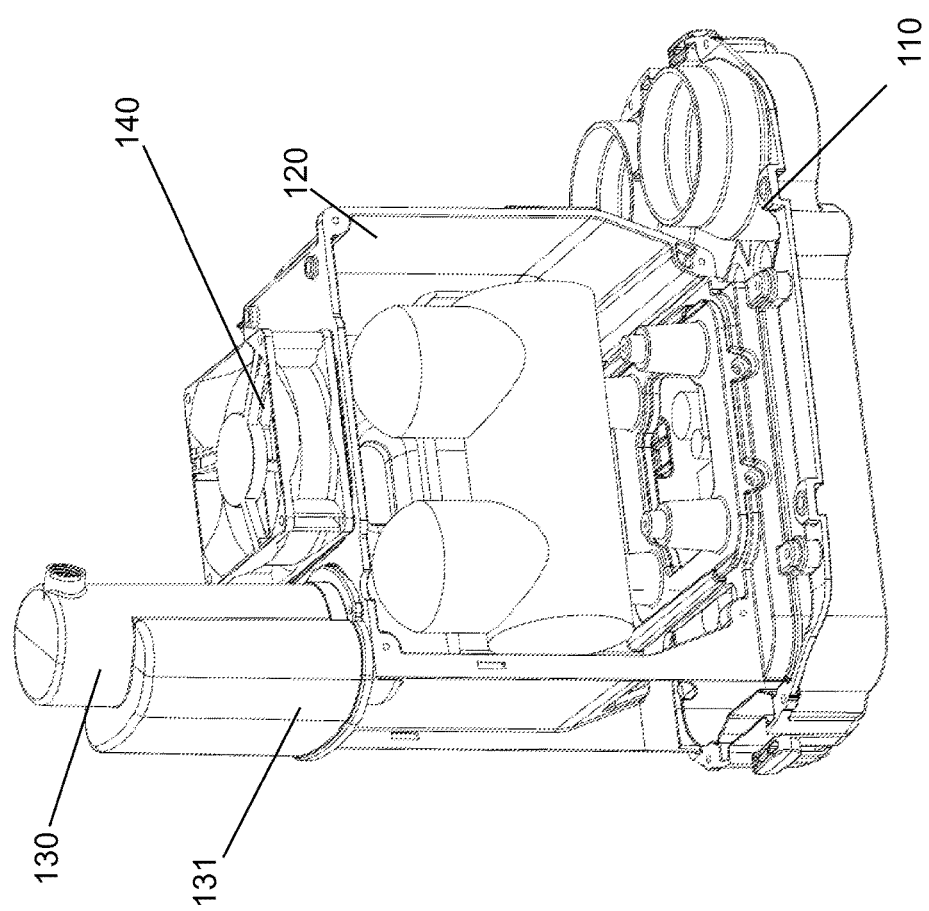
FIG. 4 illustrates an exemplary modular design of the concentrator.
Figure 5:
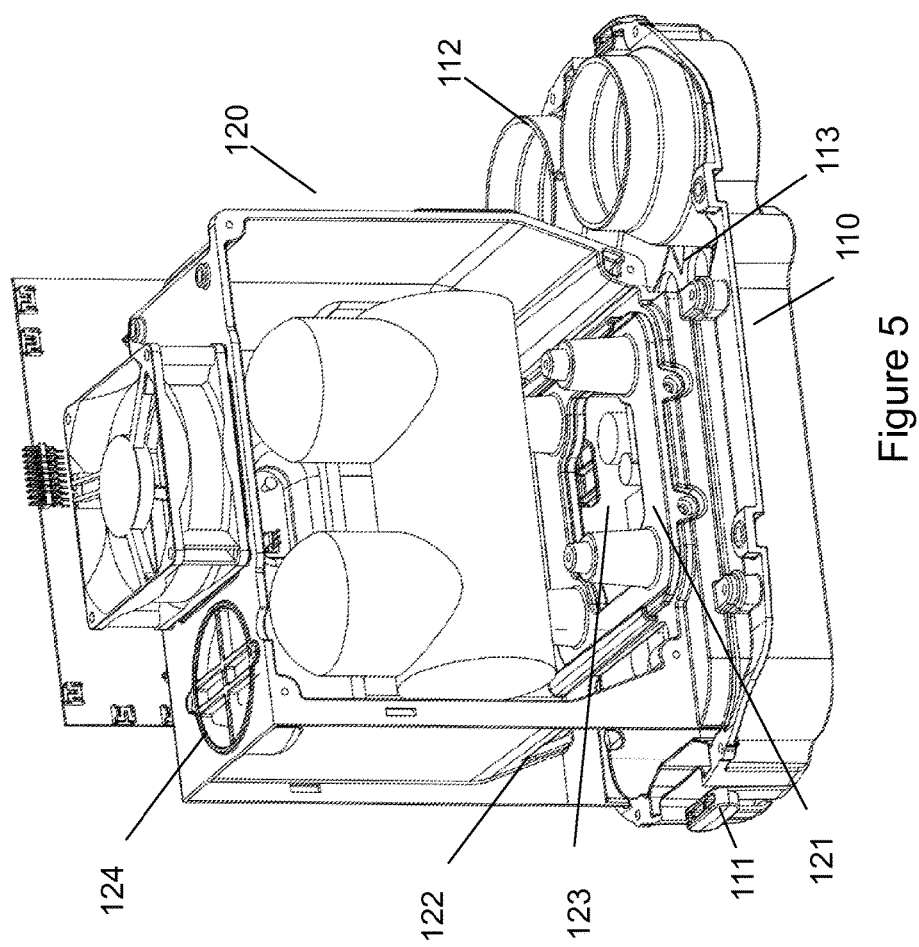
FIG. 5 illustrates additional exemplary elements of the concentrator.

FIG. 4 illustrates internal elements of the novel concentrator. The concentrator includes two modules, the compressor module 120 and the Power supply/bed dock module 110. Blower 140 is part of the compressor module 120 as are silencing elements exhaust muffler 130 and compressor intake silencer 131. Since the predominance of the noise from the concentrator originates at the compressor intake, the intake silencer is located between the compressor and the externally mounted air filter to prevent noise being communicated to the exterior of the concentrator. The muffler likewise must handle the large volume of gas generated when an adsorber is exhausted. This exhaust gas is routed into the compressor chassis to maximally contain the exhaust sound and to prevent the nitrogen rich exhaust gas from being recycled into the compressor intake. Referring to FIG. 5, the compressor is mounted to a modular load dispersing element 121 to prevent chassis damage during shipment. This structure has a high surface area interface to the chassis and prevents the fasteners from being load concentrating elements by utilizing a sliding rail system to retain the structure in multiple orientations. The load dispersing element 121 also contains cooling ducts 123 from the compressor module to the power supply module to ensure the cooling fan is actively cooling the power supply. The compressor module contains exhaust gas ducting 124 to the muffler as well as compressor cooling ducting 122. The power supply/bed dock module 110 contains the adsorber alignment guides 112, adsorber retention latches 113 and the lower housing (boot) latches 111. The bed retention system may be one of several forms, such as those described in application Ser. No. 13/016,706

Figure 6:
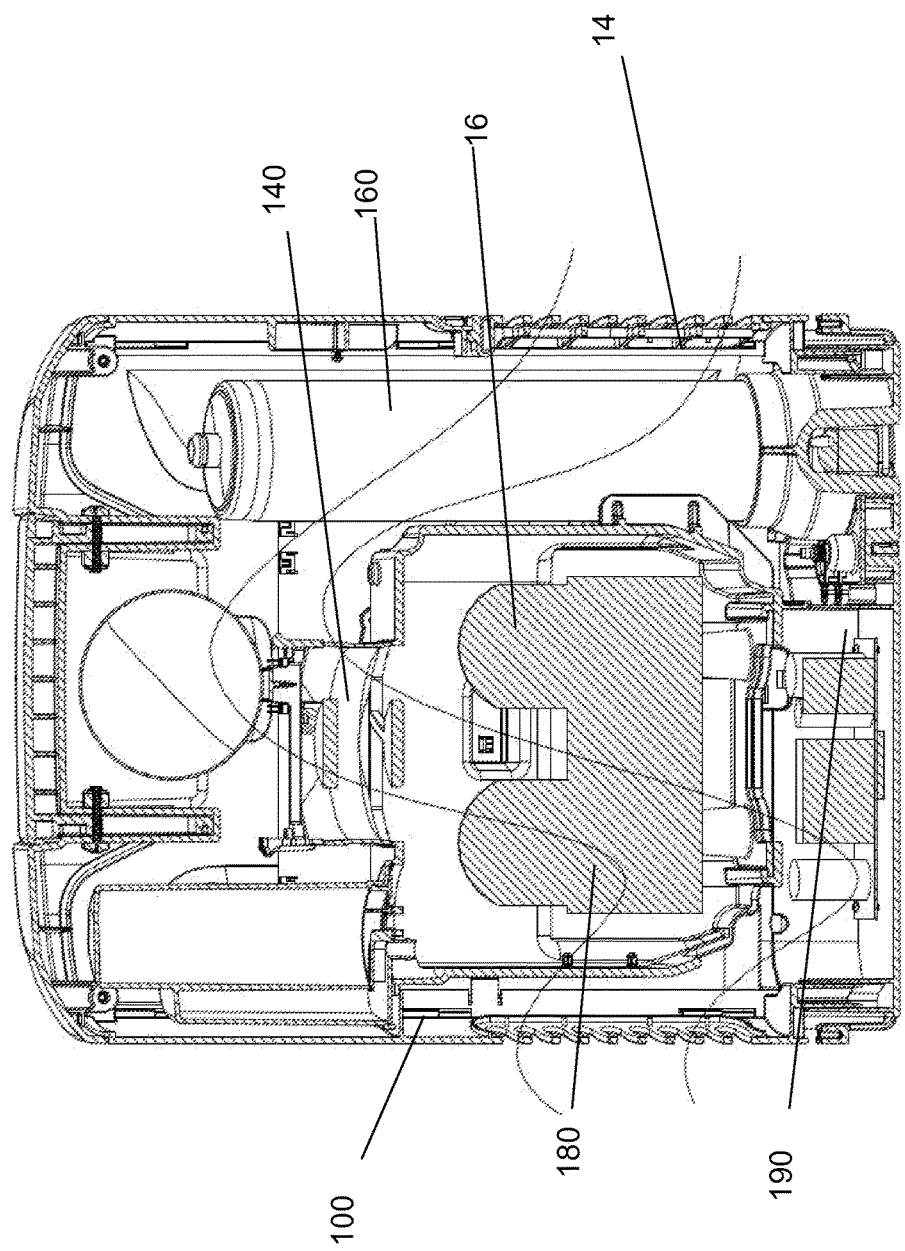
FIG. 6 depicts the novel open airflow design of the concentrator.
Figure 7:
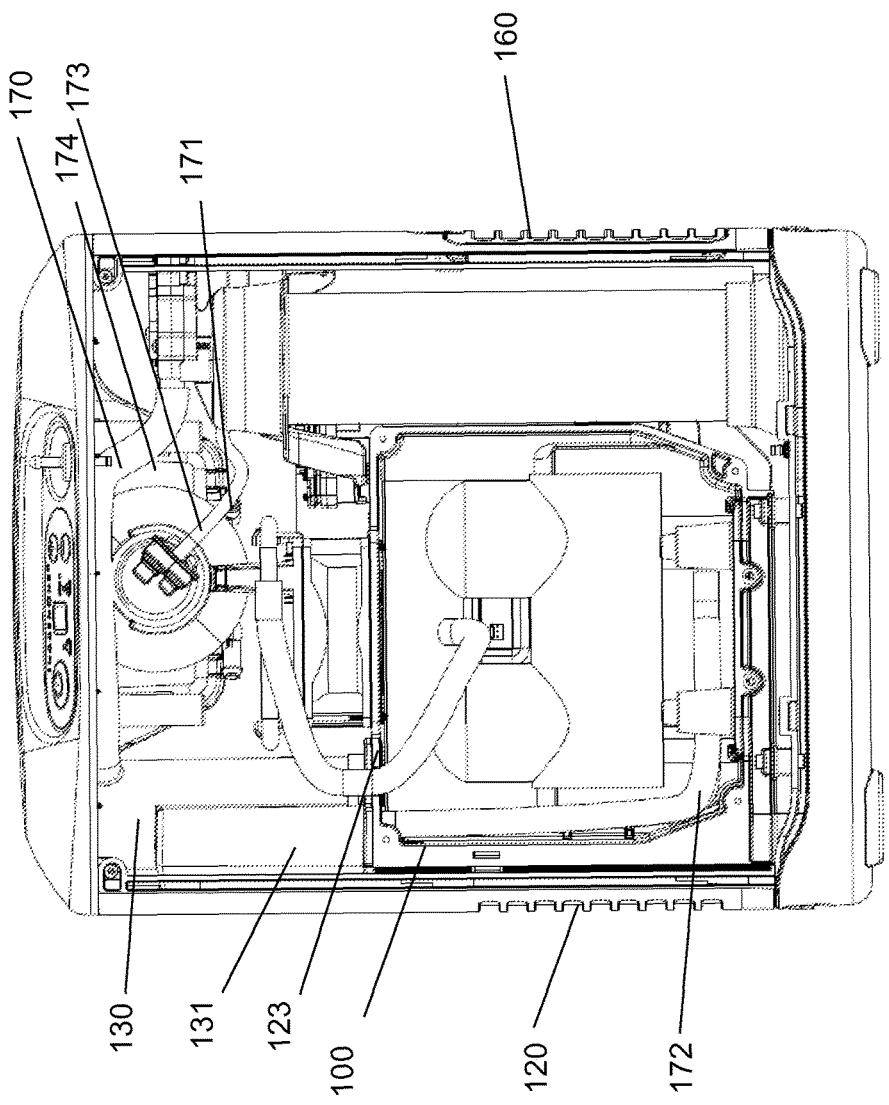
FIG. 7 illustrates the novel air connection design of the concentrator.

FIGS. 6 and 7 illustrate the unitary cooling/acoustic damping airflow system of the concentrator 100. FIG. 6 illustrates the open flow portion of the air system. Blower 140 intakes air from the intake gross particle filter 14 in a tortuous path over the adsorbent beds 160. This air path ensures that the adsorbent beds are cooled with the coolest possible air and that the heat generated from the compressor 180 and power supply 190 is not directed back to other components in the system. The blower discharge air is directed over the compressor heads and cylinders 16 which are the most temperature sensitive parts of the system. The cooling air then passes over the compressor 180 motor and power supply 190 before being expelled out the exhaust to minimize the heat build up in the system and minimize the escaping noise through the vents. This progressive cooling system ensures that the sensitivity of the component to heat is commensurate with its location in the cooling air path. The cooling layout is also optimized to ensure that heat buildup occurs near the exhaust exit to minimize heat retention in the system and thermal heating of non-heat generating components such as the valves and circuit board.

The concentrator 100 piped airflow portion is shown in FIG. 7. Intake connection 171 collects ambient air as it is drawn in through the gross particle filter and air inlet 160 and draws it into the compressor air filter 174. The intake air is routed to intake silencer 131 from the compressor air filter whose output is routed to the compressor by compressor connector 172. Bed product gas is routed toward patient by connection 173, while exhaust gas is routed to muffler 130 by connection 170. Muffler output is vented 123 to the compressor module as shown in FIG. 5 location 124. Where it is pushed to the panel outlet by the open airflow through the compressor module 120. Thus the blower is the single point of origin for the unitary air system, which includes silencing elements for both compressor input and exhaust output, as well as comprehensive cooling and exhaust gas management.

Figure 8:
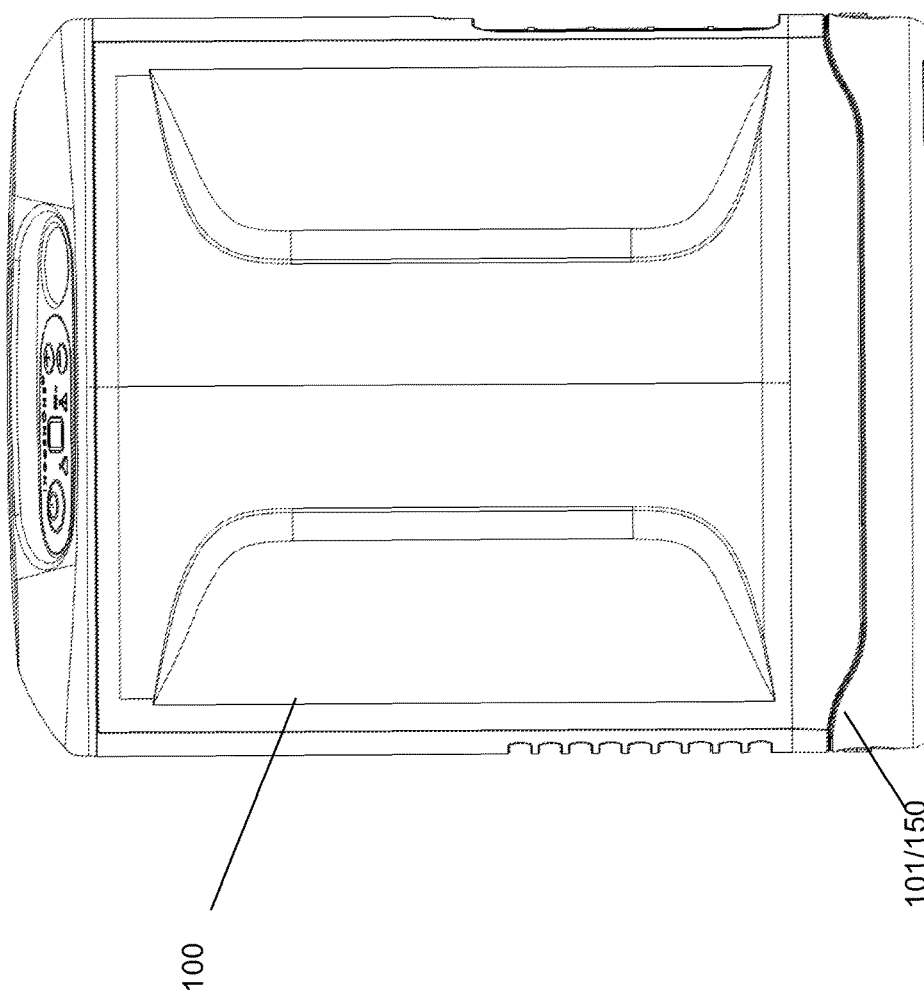
FIG. 8 depicts a protective covering for the power supply/bed module.

FIG. 8 illustrates an embodiment which may include a removable protective boot 150 which fits over the bottom panel 101. This boot preferably is easily removable, by the user, and when removed provides access to the beds and bed retention mechanisms. Thus the beds may be removed and replaced simply by removing the boot with no other disassembly required. The boot may optionally include isolation feet and/or wheels. As was shown in FIG. 5 the adsorber and power supply subchassis 110 houses the power supply and the adsorber mounting, two of the critical components of the oxygen concentrator covered by lower housing component 101. To ensure that these components are protected from external damage or contamination from water and debris, the lower housing component 101 in FIG. 8 is a snap on cover that offers protection to the internal components of the power supply and adsorber subchassis. Optional rubber isolation feet 102 are depicted in FIG. 3 to ensure that the vibration and noise from the concentrator are not rigidly coupled to the floor or other operating surface of the concentrator. The removable lower housing can be removed by the user to access and change the adsorbent beds. Therefore, the removal of the lower housing without tools is important to allow the user to change the adsorbent beds rather than a technician or service provider.

Figure 9:
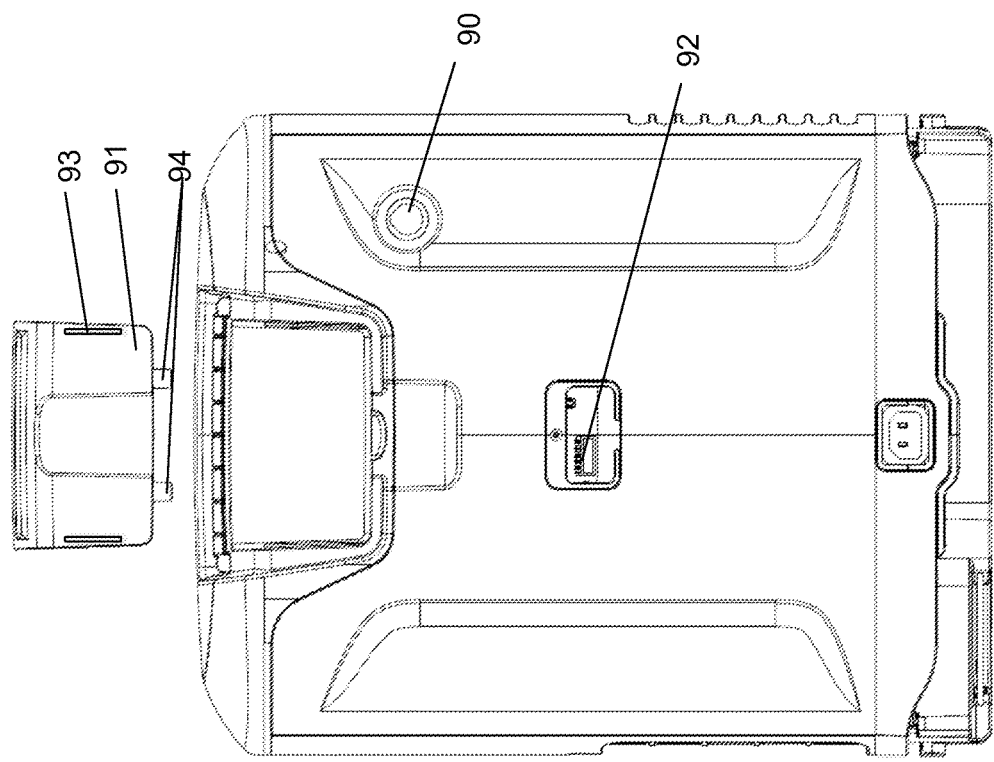
FIG. 9 depicts an exemplary view of the external power supply input, air filter, and diagnostics port of the concentrator.

FIG. 9 illustrates how the preferred embodiment of the improved stationary concentrator includes the adaptability of an alternate power input port 90 designed to operate the system on DC input power. The DC power may be supplied by an external battery system or other DC power source such as a vehicle. In this preferred embodiment, the power input connector includes at least one communication line to facilitate identification of the type and configuration of the DC power source. This is the preferred embodiment because it allows for flexible power moding such that the concentrator may restrict its allowed flow settings to match the available power of the DC power source. For example, a standard automobile power outlet may supply only 120 W and the concentrator may limit operation to 3 LPM or less to prevent malfunction or damage to the DC power source. Whereas the presence of a larger external battery or power supply may allow full range operation and the information communicated between the power source and the concentrator's DC input system can allow for this optimized operation.

In another embodiment of the improved stationary concentrator, there is a diagnostic interface 92 located on the rear panel of the concentrator as seen in FIG. 9. This connector serves a range of purposes that may include providing a display output to show additional information about the internal operating conditions of the concentrator. The diagnostic connector may also include other functionality such as a USB interface or software update port that was previously a discreet output on portable oxygen concentrators where cost is less of a concern. This diagnostic port connector allows for cost to be removed from the host concentrator system and moved to a diagnostic interface system such that the cost is not incurred on every concentrator.

The preferred embodiment depicted in FIG. 9 additionally includes an externally mounted air intake filter 91 that feeds air into the compressor. The topside external location of this filter allows easy access by the user to check the dirt loading of the filter and to replace the filter as needed without the assistance of a technician or service provider. Unlike other stationary concentrators that locate the filter behind a trap door, the filter 91 depicted in FIG. 9 does not require any opening of the concentrator for access. The filter further includes a clear housing component that allows direct visual evaluation of the filter element by the user so that the replacement of the filter can be limited by need rather than specified at discrete or predetermined intervals of time or run hours. The topside location also allows ease of access to the user so that the user does not have to kneel down of lift the concentrator up to access the filter for inspection or replacement. In a preferred embodiment the air filter may form an ornamental portion of the concentrator case and my include features such as slots 93 to mount the humidifier accessory to the concentrator. This mounting location ensures the filter is located in a commonly accessed location. This specific configuration also ensures that any damage to the humidifier mount can be replaced by replacing the user replaceable intake filter thus avoiding a repair by a technician or service provider.

The inlet filter depicted in FIG. 9 is directed to intake ambient air into the compressor system from the intake side of the air blower. This optimal configuration ensures that the compressor receives cool ambient air that is free from concentrated nitrogen because the exhaust gas is directed into the exhaust side chamber of the air blower. The air inlet configuration depicted in FIG. 9 further contributes to low noise operation because the intake filter ports 94 are directed into the interior of the concentrator so that the intake valve noise from the compressor that escapes back through the filter element and housing is not directed to the exterior of the concentrator where it would be more audible to the user.

In an optional configuration, the lower housing 101 depicted in FIG. 3 can also be modified to meet specific user needs and can be easily swapped during any stage of manufacturing or deployment of the concentrator since the lower housing can be removed and replaced without tools. For example, the rubber vibration isolation feet 102 can be substituted for caster wheels or a battery cart mounting system in alternate configurations. The changeable lower housing serves to allow the concentrator to serve a multitude of purposes as well as providing for easy replacement in the case of damage. A common failure mode or prior art stationary concentrator is the caster wheels being broken during shipping, transport or usage. When these caster wheels are broken, the entire housing must be replaced since the housings are typically composed of large clamshell type enclosures or intricate lower housings that are integrated to such other components such as compressor mounts or internal chassis. The separate and simple lower housing in the invention further simplifies service, configuration, and maintenance of the concentrator while in service and reduces the need to remove the concentrator from service to perform repairs.

The foregoing description of the preferred embodiments of the present invention has shown, described and pointed out the fundamental novel features of the invention. It will be understood that various omissions, substitutions, and changes in the form of the detail of the apparatus as

We claim:

1. A portable oxygen concentrator platform, comprising:
   at least one of a PSA, VPSA or VSA core section capable of mating with user replaceable adsorbers comprising;
   a housing,
   a controller,
   a user interface,
   at least two user replaceable adsorber beds,
   at least one compressor, control valve, and air filter, comprising a PSA/VPSA/VSA oxygen system when mated with the user replaceable adsorbers,
   a patient delivery apparatus,
   an airblower
   a power supply and bed dock module comprising at least one AC-DC power supply and at least one bed dock for the user replaceable adsorber beds wherein the bed dock comprises feed gas connectors, product gas connectors, and bed retention mechanisms; and,
   a compressor module comprising the compressor and a compressor mount, along with the airblower, wherein;
   the power supply and bed dock module and the compressor module are configured to mate together, and when mated the combined modules and housing are configured to form a unitary cooling and acoustic damping air flow system and to direct cooling air over at least the adsorbent beds, compressor, and the AC-DC power supply;
   wherein the portable oxygen concentrator weighs less than 25 pounds, produces less than 50 dBA acoustic noise when operating, and has an output gas flow of 5 lpm or less.

2. The concentrator of claim 1 comprising an input to receive the output from an external rechargeable battery capable of running the concentrator for greater than 2 hours.

3. The concentrator of claim 2 wherein the concentrator may be switched between operating from the internal AC-DC power supply and the external battery.

4. The concentrator of claim 1 further comprising a compressor inlet filter mounted to an exterior of the concentrator.

5. The concentrator of claim 4 wherein the inlet and outlet of the compressor air filter are connected to an interior of the concentrator.

6. The concentrator of claim 4 wherein the compressor inlet filter forms an ornamental surface of the exterior.

7. The concentrator of claim 4 wherein the compressor inlet filter forms a portion of a humidifier mount.

8. The concentrator of claim 1 wherein the compressor module is interconnected to the power supply and bed dock module via rails to provide a high amount of surface engagement to distribute shock load and prevent breakage of a chassis.

9. The concentrator of claim 1 wherein the power supply and bed dock module mates to a removable lower housing component comprising at least one of rubber vibration and noise isolating feet or wheels.

10. The concentrator of claim 1 comprising an intake silencer and wherein the intake silencer and an exhaust muffler are a common structure.

11. The concentrator of claim 9 wherein the lower housing component can be removed to access the replaceable adsorber beds.

12. The concentrator of claim 1 further comprising a diagnostics interface.

13. The concentrator of claim 12 wherein the diagnostics interface is externally accessible.

14. The concentrator of claim 13 wherein the diagnostics interface mates to an external readout when the concentrator is serviced.

* * * * *